(12) United States Patent
Lee

(10) Patent No.: US 12,121,073 B2
(45) Date of Patent: Oct. 22, 2024

(54) PRESSURIZATION DEVICE FOR AEROSOL GENERATING ARTICLE AND AEROSOL GENERATING SYSTEM INCLUDING THE SAME

(71) Applicant: KT&G CORPORATION, Daejeon (KR)

(72) Inventor: Moon Bong Lee, Seoul (KR)

(73) Assignee: KT&G CORPORATION, Daejeon (KR)

( * ) Notice: Subject to any disclaimer, the term of this patent is extended or adjusted under 35 U.S.C. 154(b) by 442 days.

(21) Appl. No.: 17/606,843

(22) PCT Filed: Jun. 28, 2021

(86) PCT No.: PCT/KR2021/008103
§ 371 (c)(1),
(2) Date: Oct. 27, 2021

(87) PCT Pub. No.: WO2022/014899
PCT Pub. Date: Jan. 20, 2022

(65) Prior Publication Data
US 2023/0145606 A1 May 11, 2023

(30) Foreign Application Priority Data

Jul. 17, 2020 (KR) .................. 10-2020-0089218
Sep. 23, 2020 (KR) .................. 10-2020-0123328

(51) Int. Cl.
*A24F 42/10* (2020.01)
*A24D 1/20* (2020.01)
*A24F 42/60* (2020.01)

(52) U.S. Cl.
CPC ............ *A24F 42/10* (2020.01); *A24D 1/20* (2020.01); *A24F 42/60* (2020.01)

(58) Field of Classification Search
CPC ........... A24D 1/20; A24F 42/60; A24F 42/10
(Continued)

(56) References Cited

U.S. PATENT DOCUMENTS 1,607,872 A * 11/1926 Cooper ............... A01M 23/265
43/88
5,865,186 A 2/1999 Volsey, II
(Continued)

FOREIGN PATENT DOCUMENTS

EP    2 191 735 A1   6/2010
JP    5-39882 U      5/1993
(Continued)

OTHER PUBLICATIONS

International Search Report for PCT/KR2021/008103 dated Sep. 30, 2021.
(Continued)

*Primary Examiner* — Abdullah A Riyami
*Assistant Examiner* — Vladimir Imas
(74) *Attorney, Agent, or Firm* — Sughrue Mion, PLLC

(57) ABSTRACT

A pressurization device, for pressurizing an aerosol generating article, includes: a pressurization portion that is configured to be moved by a force applied by the aerosol generating article such that the pressurization portion pressurizes the aerosol generating article to induce a chemical reaction that generates an aerosol inside the aerosol generating article.

19 Claims, 9 Drawing Sheets

(58) Field of Classification Search
USPC .......................................................... 131/329
See application file for complete search history.

(56) References Cited

U.S. PATENT DOCUMENTS

| | | | | |
|---|---|---|---|---|
| 7,117,867 | B2* | 10/2006 | Cox | ........................ A24F 40/60 |
| | | | | 128/200.14 |
| 10,251,421 | B2 | 4/2019 | Kieslich | |
| 11,213,635 | B2 | 1/2022 | Hepworth et al. | |
| 11,677,201 | B2* | 6/2023 | Novak, III | ............ A61M 15/06 |
| | | | | 131/329 |
| 2015/0313286 | A1 | 11/2015 | Koller | |
| 2019/0106268 | A1 | 4/2019 | Sebastian et al. | |
| 2019/0281898 | A1 | 9/2019 | Hopps et al. | |
| 2020/0163380 | A1 | 5/2020 | Lee et al. | |
| 2021/0059301 | A1* | 3/2021 | Hejazi | ..................... A24F 42/20 |
| 2023/0105938 | A1* | 4/2023 | Yoon | ..................... B05B 7/1686 |
| | | | | 131/329 |
| 2023/0292820 | A1* | 9/2023 | Soffe | ....................... A24F 40/20 |
| | | | | 131/359 |

FOREIGN PATENT DOCUMENTS

| | | | |
|---|---|---|---|
| JP | 2019-528717 | A | 10/2019 |
| KR | 20120093505 | A | 8/2012 |
| KR | 10-2016-0085965 | A | 7/2016 |
| KR | 10-2017-0135043 | A | 12/2017 |
| KR | 10-2018-0070445 | A | 6/2018 |
| KR | 10-2020-0005081 | A | 1/2020 |
| WO | 2014/039308 | A1 | 3/2014 |
| WO | 2014/045024 | A2 | 3/2014 |

OTHER PUBLICATIONS

Written Opinion for PCT/KR2021/008103 dated Sep. 30, 2021.
Extended European Search Report dated Apr. 8, 2022 in European Application No. 21783379.7.
Korean Office Action dated Sep. 23, 2022 in Korean Application No. 10-2020-0123328.
Japanese Office Action dated Nov. 8, 2022 in Japanese Patent Application No. 2021-568966.

* cited by examiner

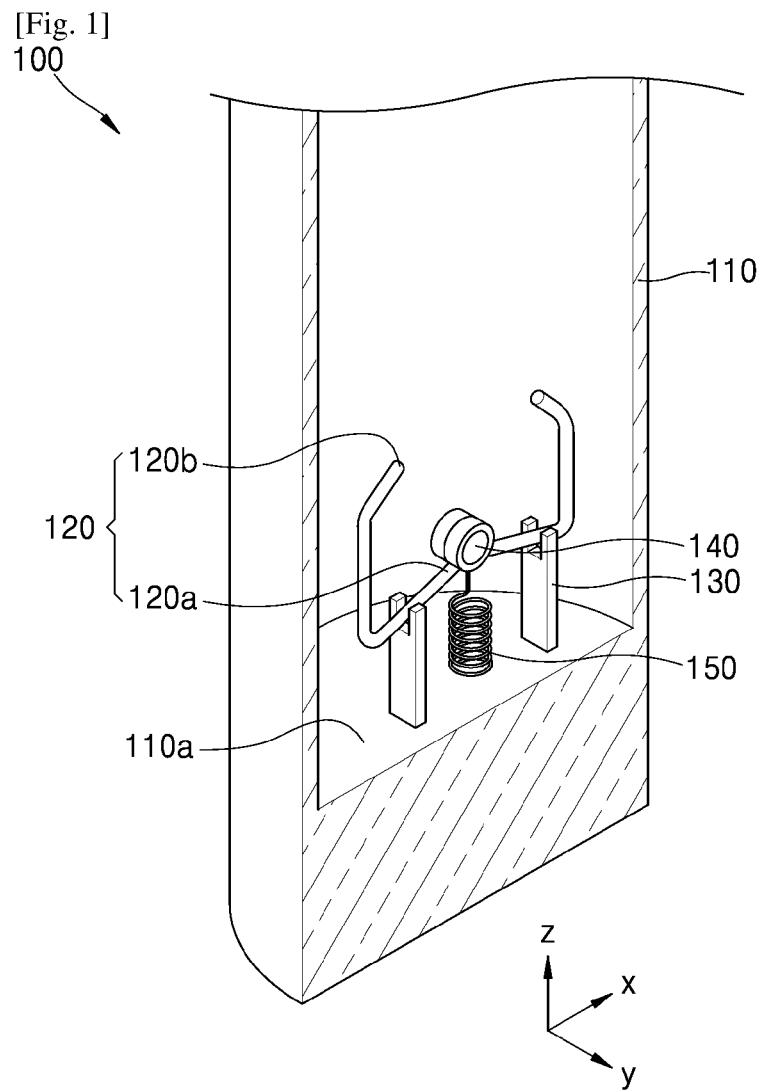

[Fig. 2A]
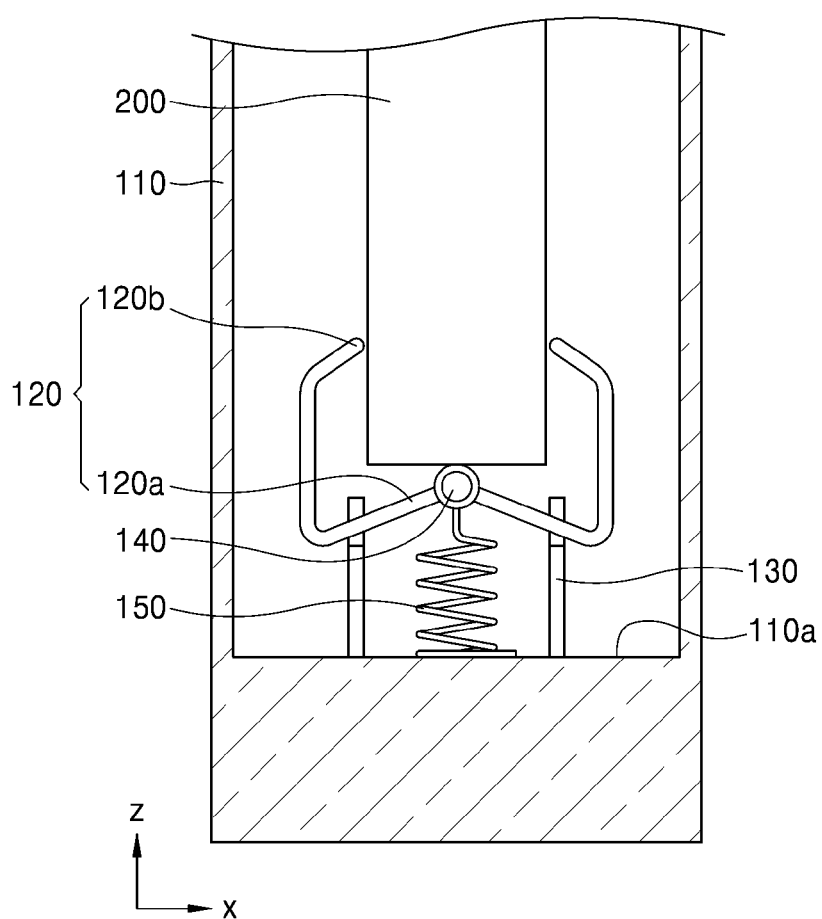

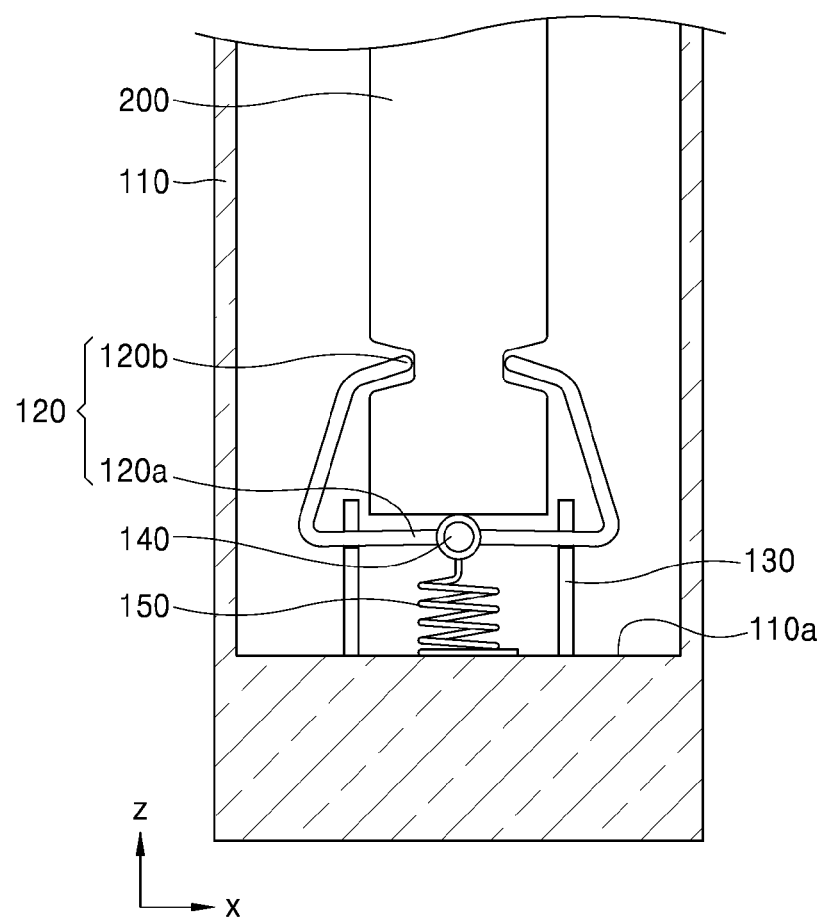
[Fig. 2B]

[Fig. 3A]
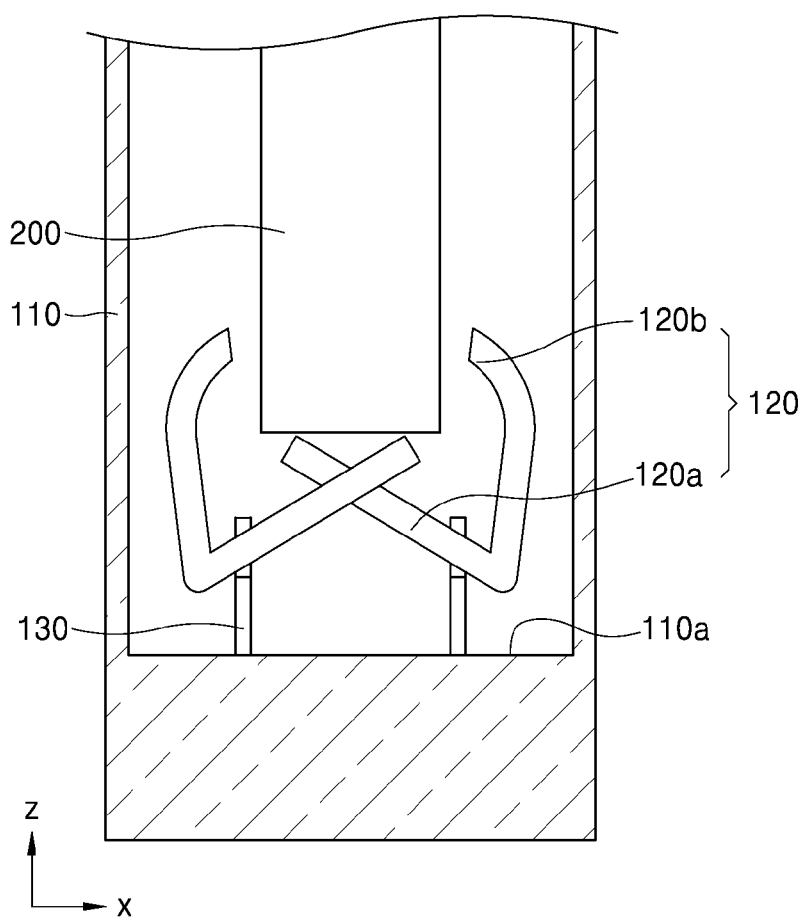

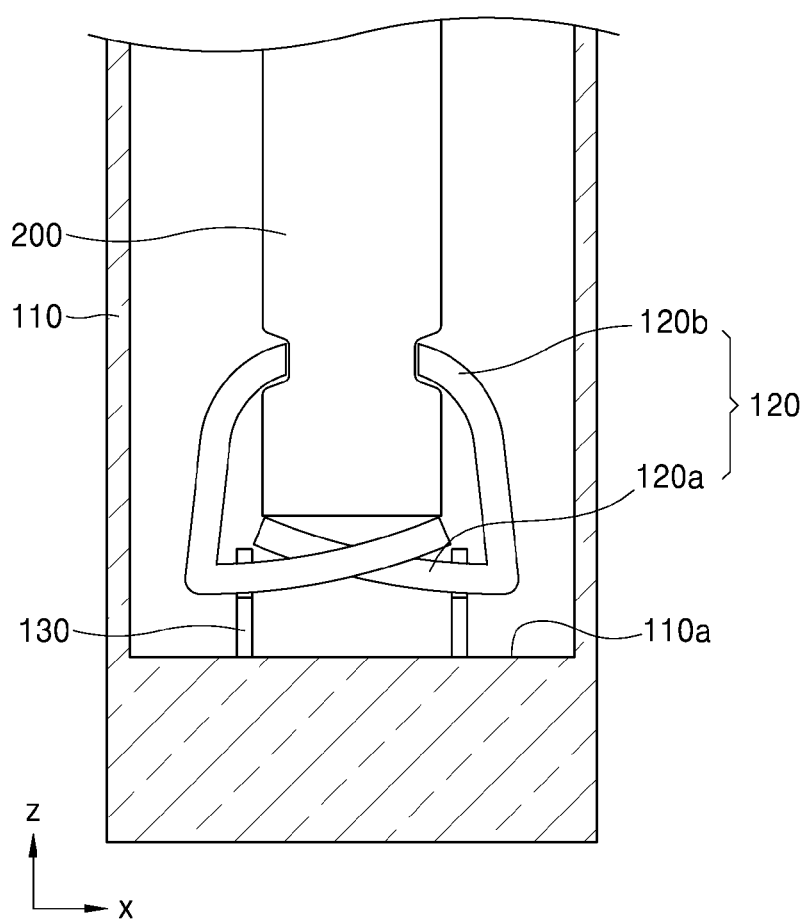
[Fig. 3B]

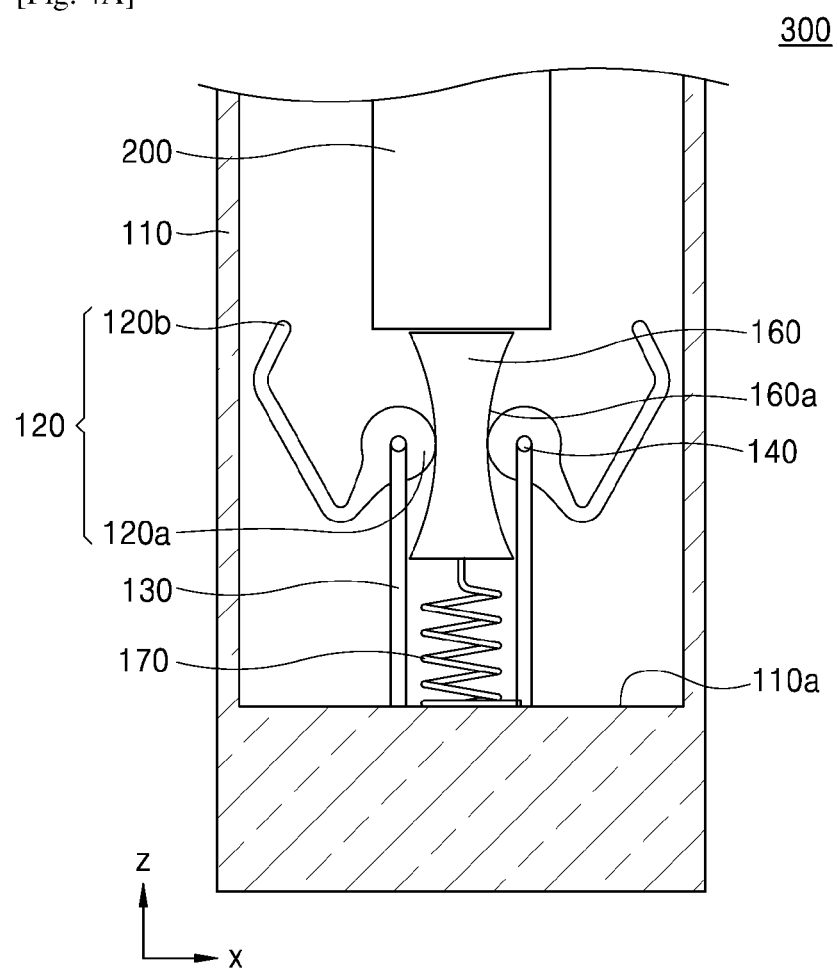
[Fig. 4A]

[Fig. 4B]
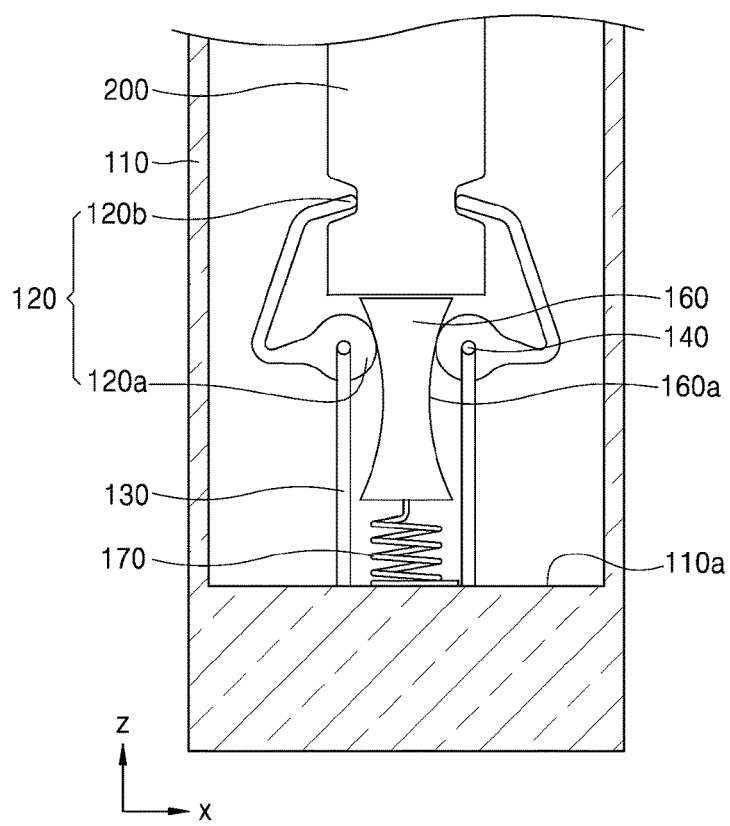
[Fig. 5A]
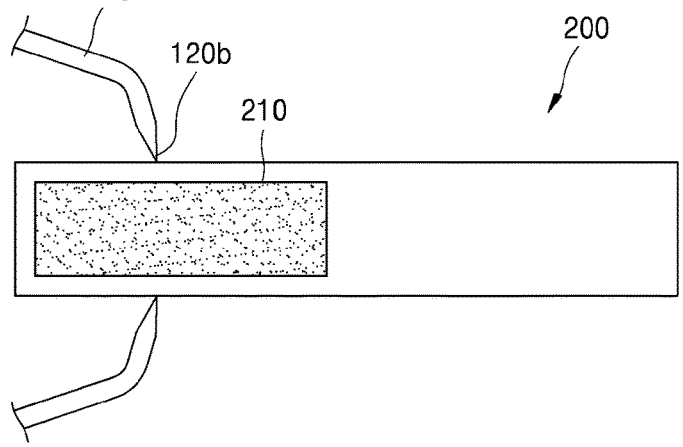
[Fig. 5B]
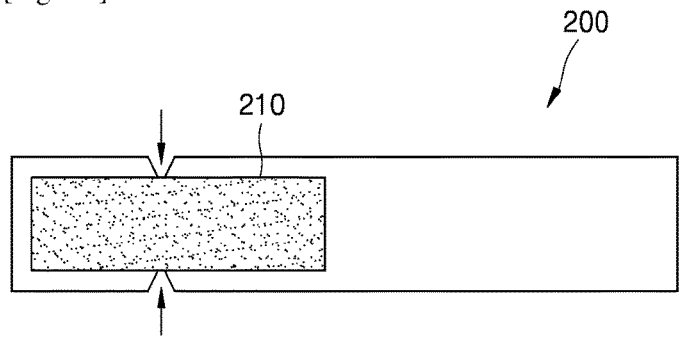

[Fig. 6A]
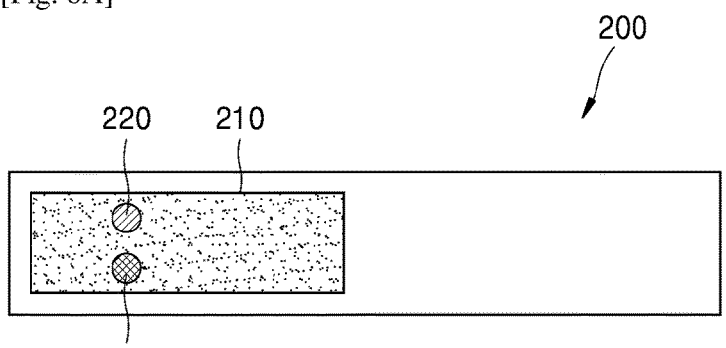
[Fig. 6B]
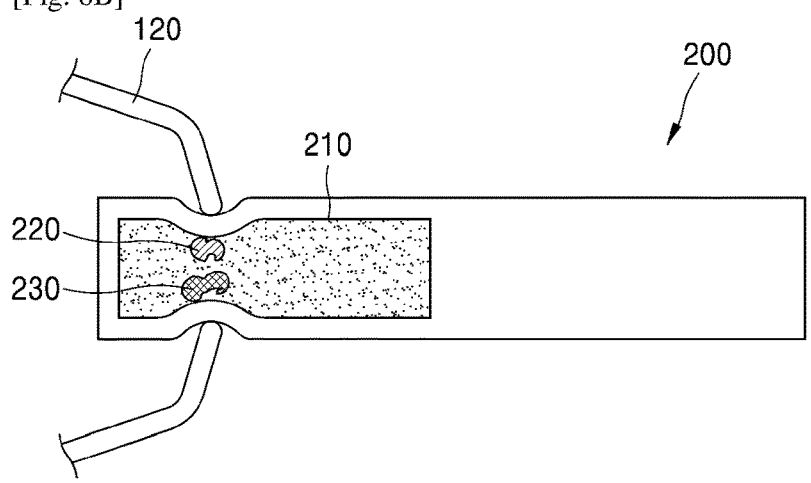
[Fig. 7A]
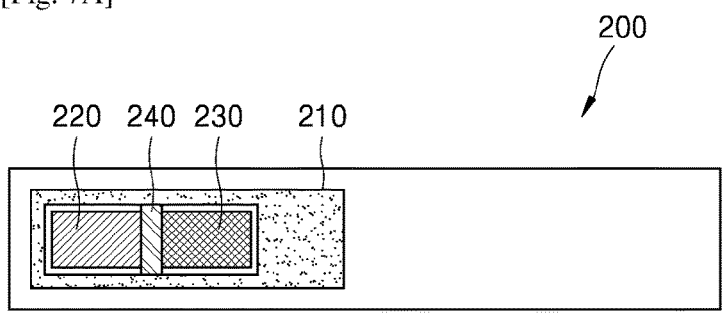
[Fig. 7B]
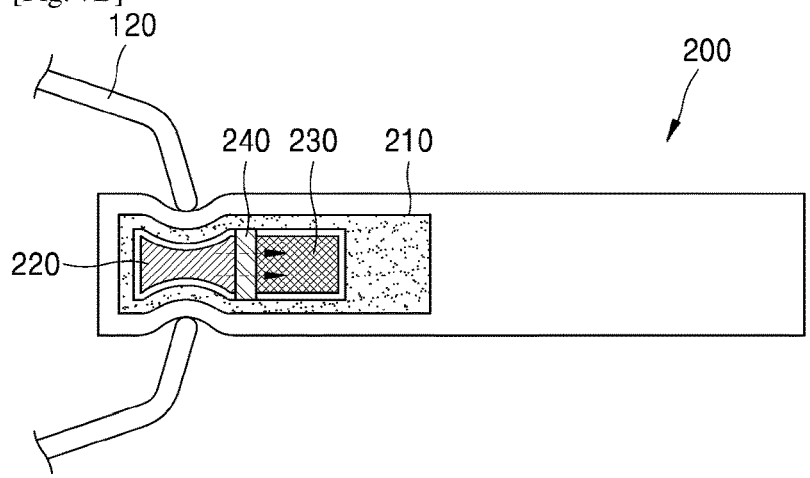

[Fig. 8A]
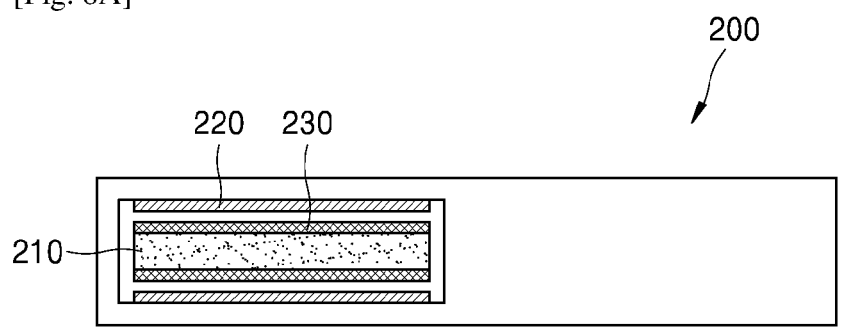
[Fig. 8B]
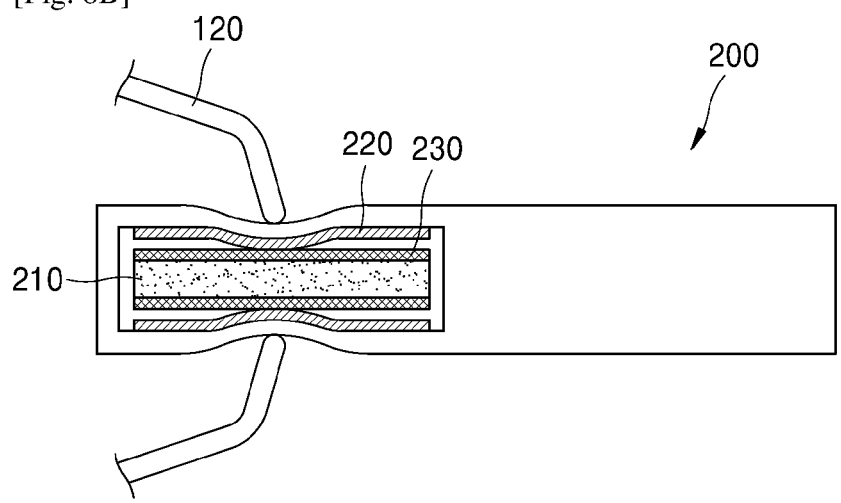

PRESSURIZATION DEVICE FOR AEROSOL GENERATING ARTICLE AND AEROSOL GENERATING SYSTEM INCLUDING THE SAME

CROSS REFERENCE TO RELATED APPLICATIONS

This application is a National Stage of International Application No. PCT/KR2021/008103 filed Jun. 28, 2021, claiming priority based on Korean Patent Application No. 10-2020-0089218 filed Jul. 17, 2020 and Korean Patent Application No. 10-2020-0123328 filed Sep. 23, 2020.

TECHNICAL FIELD

Embodiments of the present disclosure relate to a pressurization device for an aerosol generating article and an aerosol generating system including the pressurization device, and more particularly, to a pressurization device for an aerosol generating article to induce a chemical reaction for generating an aerosol, and an aerosol generating system including the pressurization device.

BACKGROUND ART

There is an increasing demand for an aerosol generating device that generates an aerosol in a non-combustion manner by replacing a method of generating an aerosol by burning a cigarette. An aerosol generating device generates an aerosol from an aerosol generating substance in a non-combustible manner and supplies the aerosol to a user, or generates an aerosol having a flavor by passing a vapor generated from an aerosol generating substance through an aroma medium.

Thus, since the conventional aerosol generating device generates the aerosol from the aerosol generating substance by using electric power, the user might be inconvenienced due to periodically recharging the aerosol generating device. Accordingly, the demand for a method capable of supplying an aerosol to a user without use of electric power has increased.

DISCLOSURE

Technical Problem

A conventional aerosol generating device utilizes power to generate an aerosol from an aerosol generating substance. Accordingly, a user may feel inconvenience of periodically checking a remaining amount of power of the aerosol generating device and recharging the aerosol generating device in order to inhale the aerosol.

Technical problems to be solved by the embodiments are not limited to the above-described problems, and problems that are not mentioned will be clearly understood by those of ordinary skill in the art from the present disclosure and the accompanying drawings.

Technical Solution

As a technical means for solving the technical problems described above, according to an embodiment, there is provided a pressurization device for an aerosol generating article, the pressurization device pressurizing the aerosol generating article and including: a pressurization portion that is moved by a force applied by the aerosol generating article and pressurizes the aerosol generating article to induce a chemical reaction for generating an aerosol inside the aerosol generating article.

According to another embodiment, there is provided an aerosol generating system including: an aerosol generating article that includes a first substance for generating an aerosol and a second substance for generating an aerosol, the second substance being different from the first substance; and a pressurization device for an aerosol generating article including a pressurization portion that is moved by a force applied by the aerosol generating article and pressurizes the aerosol generating article to induce a chemical reaction in at least one of the first substance and the second substance.

According to embodiments, a pressurization device for an aerosol generating article is provided that induces a chemical reaction for generating an aerosol, and an aerosol generating system is provided.

Advantageous Effects

The pressurization device for an aerosol generating article and the aerosol generating system according to embodiments of the present disclosure may pressurize the aerosol generating article and induce a chemical reaction for generating the aerosol inside the aerosol generating article to provide the aerosol to a user.

The effects according to one or more embodiments are not limited to the effects described above, and unmentioned effects will be clearly understood by one of ordinary skill in the art from the present specification and the accompanying drawings.

DESCRIPTION OF DRAWINGS

FIG. 1 is a view illustrating a pressurization device for an aerosol generating article according to an embodiment.

FIG. 2A is a view illustrating an aerosol generating system according to another embodiment.

FIG. 2B is a sectional view illustrating another aspect of the aerosol generating system illustrated in FIG. 2A.

FIG. 3A is a view illustrating an aerosol generating system according to another embodiment.

FIG. 3B is a view illustrating another aspect of the aerosol generating system illustrated in FIG. 3A.

FIG. 4A is a view illustrating an aerosol generating system according to another embodiment.

FIG. 4B is a sectional view illustrating another aspect of the aerosol generating system illustrated in FIG. 4A.

FIG. 5A is a view illustrating an example wherein an aerosol generating article according to another embodiment is pressurized by a pressurization portion.

FIG. 5B is a view illustrating an example of a state after the aerosol generating article illustrated in FIG. 5A is pressurized by the pressurization portion.

FIG. 6A is a view illustrating an aerosol generating article according to another embodiment.

FIG. 6B is a view illustrating an example of another aspect in which the aerosol generating article illustrated in FIG. 6A is pressurized by a pressurization portion.

FIG. 7A is a view illustrating an aerosol generating article according to another embodiment.

FIG. 7B is a view illustrating an example wherein the aerosol generating article illustrated in FIG. 7A is pressurized by a pressurization portion.

FIG. 8A is a view illustrating an aerosol generating article according to another embodiment.

FIG. 8B is a view illustrating an example wherein the aerosol generating article illustrated in FIG. 8A is pressurized by a pressurization portion.

BEST MODE

According to an embodiment, a pressurization device for pressurizing an aerosol generating article is provided. The pressurization device includes a pressurization portion that is configured to be moved by a force applied by the aerosol generating article such that the pressurization portion pressurizes the aerosol generating article to induce a chemical reaction that generates an aerosol inside the aerosol generating article.

One end of the pressurization portion may be configured to receive the force applied by the aerosol generating article, such that the pressurization portion rotates and another end of the pressurization portion pressurizes the aerosol generating article.

The pressurization device may further include a central shaft that penetrates the pressurization portion, wherein the pressurization portion rotates about the central shaft.

The pressurization device may further include an elastic member that is configured to pressurize the pressurization portion in a direction opposite to a direction in which the force is applied by the aerosol generating article to the pressurization portion.

One end of the pressurization portion may be configured to be: deformed by the aerosol generating article, when the aerosol generating article is inserted into the pressurization device, such that another end of the pressurization portion moves in a direction toward the aerosol generating article, and restored to an initial shape, when the aerosol generating article is extracted from the pressurization device, such that the other end of the pressurization portion moves in a direction away from the aerosol generating article.

The pressurization device may further include: a delivery portion that is configured to be pressurized by the aerosol generating article, such that the delivery portion moves and applies a force to the pressurization portion, wherein the pressurization portion is configured to rotate, due to the force applied by the delivery portion, such that the pressurization portion pressurizes the aerosol generating article.

The delivery portion may be in contact with the pressurization portion, and may be configured to slide with respect to the pressurization portion to rotate the pressurization portion.

One surface of the delivery portion that is in contact with the pressurization portion may be curved, such as to cause the pressurization portion to rotate by allowing the delivery portion to slide with respect to the pressurization portion.

The pressurization device may further include: an elastic member that is configured to pressurize the delivery portion in a direction opposite to a direction in which the aerosol generating article pressurizes the delivery portion.

The aerosol generating article may include a first substance and a second substance for generating an aerosol, the second substance being different from the first substance. The pressurization portion may be configured to be moved by the force applied by the aerosol generating article such that the pressurization portion pressurizes the aerosol generating article to induce a chemical reaction in at least one of the from among the first substance and the second substance.

The pressurization portion may be configured to perforate at least a part of the aerosol generating article so that external air is introduced into the aerosol generating article, and wherein the first substance may be configured to come into contact with the external air that is introduced into the aerosol generating article, such as to generate heat that heats the second sub stance.

The aerosol generating article may further include a first chamber containing the first substance, and a second chamber containing the second substance, and wherein the pressurization portion may be configured to pressurize at least one from among the first chamber and the second chamber, and allow the first substance and the second substance to come into contact with each other to induce the chemical reaction.

The first chamber and the second chamber may be disposed adjacent to each other, and wherein the aerosol generating article may further include a partition portion disposed between the first chamber and the second chamber, the partition portion may be configured to prevent contact between the first substance and the second substance.

The pressurization portion may be configured to pressurize at least one from among the first chamber and the second chamber so that the first substance or the second substance transmits through the partition portion.

The first chamber and the second chamber may be spaced apart from each other, and wherein the pressurization portion may be configured to pressurize the first chamber in a direction toward the second chamber so that the first substance and the second substance come into contact with each other.

MODE FOR INVENTION

With respect to the terms used to describe the various embodiments, the general terms which are currently and widely used are selected in consideration of functions of structural elements in the various embodiments of the present disclosure. However, meanings of the terms can be according to intention, a judicial precedence, the appearance of a new technology, and the like. In addition, in certain cases, a term which is not commonly used can be selected. In such a case, the meaning of the term will be described in detail at the corresponding portion in the description of the present disclosure. Therefore, the terms used to describe the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Meanwhile, the terms used in the present specification are for describing non-limiting example embodiments and are not intended to limit the embodiments of the present disclosure. In the present specification, a singular form also includes a plural form unless specifically stated therein.

Terms including an ordinal number such as "first" or "second" used in the present specification may be used to describe various elements, but the elements should not be limited by the terms. The ordinal terms described above may be used for the purpose of distinguishing one component from another component.

Throughout the specification, a "longitudinal direction" of a component may be a direction in which the component extends along one direction axis of the component, and the one direction axis of the component may mean to extend longer than another direction axis crossing the one direction axis.

Throughout the specification, the "embodiments" are arbitrary divisions for easily describing the invention in the present disclosure, and each of the embodiments need not be mutually exclusive. For example, the configurations disclosed in one embodiment may be applied and implemented in other embodiments, and at this time, they may be changed, applied, and implemented without departing from the scope of the present disclosure.

Hereinafter, embodiments of the present disclosure will now be described more fully with reference to the accompanying drawings, in which non-limiting example embodiments of the present disclosure are shown such that one of ordinary skill in the art may easily work the present disclosure. The embodiments of the present disclosure may, however, be embodied in many different forms and should not be construed as being limited to the examples embodiments set forth herein.

FIG. 1 is a view illustrating a pressurization device 100 for an aerosol generating article according to an embodiment.

Referring to FIG. 1, the pressurization device 100 according to an embodiment may include a housing 110, a pressurization portion 120 (e.g. at least one body configured to provide pressure), a support member 130 (e.g. a support body), a central shaft 140, and a first elastic member 150 (e.g. an elastic body).

The housing 110 may accommodate the components of the pressurization device 100 therein. In addition, the housing 110 forms an outer surface of the pressurization device 100 so that the user may easily carry the pressurization device 100 by gripping the housing 110.

A bottom surface 110a may mean a bottom surface of an inner space of the pressurization device 100 in which an external element is accommodated. For example, when the external element is inserted into the pressurization device 100, the bottom surface 110a may be a surface facing the external element.

Meanwhile, in FIG. 1, the housing 110 is illustrated to have a cylindrical shape, but is not limited thereto, and it will be apparent to those skilled in the art to which the present embodiments belong that the housing 110 may be changed into various shapes.

The pressurization portion 120 may be disposed inside the housing 110 and may be moved by a force pressurizing the pressurization portion 120. One end 120a of the pressurization portion 120 may mean a part of the pressurization portion 120 that receives a force for moving the pressurization portion 120. In addition, the other end 120b of the pressurization portion 120 may mean a part of the pressurization portion 120 that delivers a force to a pressurizing object.

Here, the expression "pressurize" may mean applying a force such as delivering pressure or impact to a specific object for deformation of a shape of the specific object or a change in a location of the specific object, and the expression may be used in the same manner in the following description.

As an example, the pressurization portion 120 may be pressurized in a first direction to move in a direction in which the external element accommodated in the pressurization device 100 is pressurized. Here, the first direction may mean a direction (for example, a −z direction in FIG. 1) from the pressurization portion 120 toward the bottom surface 110a, and the expression may be used in the same manner in the following description.

As another example, the pressurization portion 120 may be pressurized in a second direction to move in a direction away from the external element accommodated in the pressurization device 100. Here, the second direction may refer to a direction (for example, a z direction in FIG. 1) from the bottom surface 110a toward the pressurization portion 120, and the expression may be used in the same manner in the following description.

Meanwhile, in FIG. 1, the pressurization portion 120 is illustrated to include two members (e.g. bodies) that are combined, but is not limited thereto, and it will be apparent to those skilled in the art to which the present embodiments belong that the number of members included in the pressurization portion 120 may be changed.

The support member 130 may support the pressurization portion 120. For example, a groove is formed in the support member 130, and the pressurization portion 120 may be accommodated in the groove formed in the support member 130.

The support member 130 may provide a space in which the pressurization portion 120 may move on the inside of the housing 110. For example, the support member 130 may protrude from the bottom surface 110a of the housing 110 to separate the pressurization portion 120 from the bottom surface 110a. Accordingly, the support member 130 may prevent a situation in which the pressurization portion 120 does not smoothly move by coming into contact with the bottom surface 110a of the housing 110.

The central shaft 140 may be rotatably coupled with the pressurization portion 120 to provide a rotation center of the pressurization portion 120. For example, the central shaft 140 may penetrate at least a part of one end 120a of the pressurization portion 120, and the pressurization portion 120 may rotate based on the central shaft 140.

The first elastic member 150 is pressurized by the pressurization portion 120 and may provide an elastic force to the pressurization portion 120. For example, if the pressurization portion 120 is pressurized in the first direction by an external force, the first elastic member 150 may be compressed to pressurize the pressurization portion 120 in the second direction. Accordingly, when the force for pressurizing the pressurization portion 120 in the first direction decreases or disappears, the first elastic member 150 restores the position of the pressurization portion 120 by moving the pressurization portion 120 in the second direction.

For example, the first elastic member 150 may include a spring, but is not limited thereto, and various elastic bodies following Hooke's Law may be included.

In addition, the first elastic member 150 may prevent the pressurization portion 120 from being separated from the pressurization device 100. For example, the first elastic member 150 connects the bottom surface 110a and one end 120a of the pressurization portion 120 so that the pressurization portion 120 may be prevented from being separated from the pressurization device 100.

FIG. 2A is a view illustrating an aerosol generating system 300 according to another embodiment, and FIG. 2B is a sectional view illustrating another aspect of the aerosol generating system 300 illustrated in FIG. 2A.

In detail, FIG. 2A is a view illustrating an aspect in which an aerosol generating article 200 is inserted into the pressurization device 100, and FIG. 2B is a view illustrating an aspect in which the pressurization device 100 pressurizes the aerosol generating article 200.

The aerosol generating system 300 according to an embodiment may include the pressurization device 100 and the aerosol generating article 200.

The aerosol generating article 200 may generate the aerosol through a chemical reaction induced by being pressurized by the pressurization device 100. For example, the chemical reaction that occurs inside the aerosol generating article 200 may include an exothermic reaction in which a predetermined substance heats the aerosol generating substance to generate an aerosol, an acid-base reaction in which an acid substance and a base substance react to form the aerosol, or the like, and detailed description will be provided later.

The user may insert the aerosol generating article 200 into the inside of the pressurization device 100 to inhale the aerosol.

The aerosol generating article 200 may pressurize one end 120a of the pressurization portion 120 in the first direction so that the other end 120b of the pressurization portion 120 pressurizes the aerosol generating article 200.

The one end 120a of the pressurization portion 120 may be pressurized by the aerosol generating article 200 and move in the first direction, thereby compressing the first elastic member 150.

In addition, while the one end 120a of the pressurization portion 120 moves in the first direction, the pressurization portion 120 may rotate in a direction in which the aerosol generating article 200 is pressurized. Accordingly, the other end 120b of the pressurization portion 120 may pressurize the aerosol generating article 200.

The pressurization portion 120 may pressurize the aerosol generating article 200 and induce the chemical reaction for generating the aerosol inside the aerosol generating article 200. Accordingly, the aerosol generating article 200 may generate the aerosol through the chemical reaction, and the generated aerosol may be inhaled by the user.

That is, the aerosol generating system 300 according to the embodiment may induce the aerosol generating article 200 to generate the aerosol via the pressurization device 100 having a simple operation structure without using power. Accordingly, the pressurization device 100 of the aerosol generating system 300 may be miniaturized so that the user may easily carry the pressurization device 100 by omitting components related to power supply such as a battery.

On the other hand, the user may reduce the force for pressurizing the aerosol generating article 200 in order to extract the aerosol generating article 200 from the pressurization device 100.

The first elastic member 150 may restore the position of the pressurization portion 120 to a state before the aerosol generating article 200 is inserted.

As an example, when the force of the user pressurizing the aerosol generating article 200 in the first direction decreases or disappears, the first elastic member 150 may move the one end 120a of the pressurization portion 120 in the second direction.

While the one end 120a of the pressurization portion 120 moves in the second direction, the other end 120b of the pressurization portion 120 may rotate in a direction away from the aerosol generating article 200. In other words, the pressurization portion 120 may be pressurized in the second direction by the first elastic member 150 and rotated in a direction away from the aerosol generating article 200 to be restored to the position as illustrated in FIG. 2A.

As described above, the aerosol generating system 300 according to the embodiment may generate the aerosol through a simple operation of inserting the aerosol generating article 200 into the pressurization device 100, and conveniently supply the aerosol to the user.

In addition, the user may easily extract the aerosol generating article 200 from the pressurization device 100 by reducing the force to pressurize the aerosol generating article 200 to prepare reuse of the pressurization device 100.

Meanwhile, the same reference numerals for the constituent elements of the embodiment illustrated in FIGS. 1 to 2B may mean the same or similar constituent elements hereinafter, and the constituent elements for one embodiment may be applied to other embodiments in substantially the same manner.

FIG. 3A is a view illustrating an aerosol generating system according to another embodiment, and FIG. 3B is a view illustrating another aspect of the aerosol generating system illustrated in FIG. 3A.

In detail, FIG. 3A is a view illustrating an aspect in which the aerosol generating article 200 is inserted into the pressurization device 100, and FIG. 3B is a view illustrating an aspect in which the pressurization device 100 pressurizes the aerosol generating article 200.

Referring to FIGS. 3A and 3B, at least a part of the pressurization portion 120 may include a material having elasticity. For example, one end 120a of the pressurization portion 120 may include a material having elasticity, thereby being pressurized and deformed by an external force, and restored when the external force disappears.

The user may insert the aerosol generating article 200 into the inside of the pressurization device 100 to inhale the aerosol.

The aerosol generating article 200 may pressurize the one end 120a of the pressurization portion 120 in the first direction so that the other end 120b of the pressurization portion 120 pressurizes the aerosol generating article 200.

The one end 120a of the pressurization portion 120 may be pressurized by the aerosol generating article 200 such that the shape of the one end 120a changes. When the one end 120a of the pressurization portion 120 is deformed, the other end 120b of the pressurization portion 120 may move in the direction in which the aerosol generating article 200 is pressurized to pressurize the aerosol generating article 200.

The pressurization portion 120 may pressurize the aerosol generating article 200 and induce the chemical reaction for generating the aerosol inside the aerosol generating article 200. Accordingly, the aerosol generating article 200 generates the aerosol through the chemical reaction, and the generated aerosol may be inhaled by the user.

The user may reduce the force for pressurizing the aerosol generating article 200 to extract the aerosol generating article 200 from the pressurization device 100.

When the force that the user uses to pressurize the aerosol generating article 200 in the first direction decreases or disappears, the one end 120a of the pressurization portion 120 may be restored in shape and the other end 120b of the pressurization portion 120 may be moved in a direction away from the aerosol generating article 200. In other words, when the shape of the one end 120a of the pressurization portion 120 is restored, the other end 120b of the pressurization portion 120 may move in a direction away from the aerosol generating article 200 to be restored to the position as illustrated in FIG. 3A.

As described above, in the aerosol generating system 300 according to the embodiment, the one end 120a of the pressurization portion 120 includes a material having elasticity, so that the user may conveniently prepare the reuse of the pressurization device 100 without a separate elastic member.

Meanwhile, in FIGS. 3A and 3B, the pressurization device 100 is illustrated to include the housing 110 and the support member 130, but it will be apparent to those skilled in the art to which the present embodiments belong that the housing 110 and the support member 130 may be omitted in some embodiments.

FIG. 4A is a view illustrating an aerosol generating system 300 according to another embodiment, and FIG. 4B is a sectional view illustrating another aspect of the aerosol generating system 300 illustrated in FIG. 4A.

In detail, FIG. 4A is a view illustrating an aspect in which the aerosol generating article 200 is inserted into the pressurization device 100, and FIG. 4B is a view illustrating an aspect in which the pressurization device 100 pressurizes the aerosol generating article 200.

Referring to FIGS. 4A and 4B, the central shaft 140, which is the rotation center of the pressurization portion 120, may be coupled to the support member 130 which is fixed to the bottom surface 110a. Accordingly, in the aerosol generating system 300 according to an embodiment, the pressurization portion 120 of the pressurization device 100 may not move in translation in the first or second direction.

The pressurization device 100 according to an embodiment may include a delivery portion 160 (e.g. a delivery body) and a second elastic member 170 (e.g. an elastic body).

The delivery portion 160 may be pressurized and moved to deliver a force to the pressurization portion 120. For example, the delivery portion 160 may pressurize the pressurization portion 120 in the first direction by moving in the first direction, or pressurize the pressurization portion 120 in the second direction by moving in the second direction.

In addition, the delivery portion 160 may be disposed to be in contact with the pressurization portion 120 and slide with respect to the pressurization portion 120 to rotate the pressurization portion 120. For example, a contact surface 160a, which is one surface of the delivery portion 160 which is in contact with one end 120a of the pressurization portion 120, may slide with respect to the pressurization portion 120 to rotate the pressurization portion 120.

As an example, the delivery portion 160 may pressurize the one end 120a of the pressurization portion 120 in the first direction by moving in the first direction. Accordingly, the pressurization portion 120 may rotate with respect to the central shaft 140 in a direction in which the aerosol generating article 200 is pressurized.

As another example, the delivery portion 160 may pressurize the one end 120a of the pressurization portion 120 in the second direction by moving in the second direction. Accordingly, the pressurization portion 120 may rotate with respect to the central shaft 140 in a direction away from the aerosol generating article 200.

The one end 120a of the pressurization portion 120 may be curved so that the contact surface 160a smoothly slides. For example, the one end 120a of the pressurization portion 120 may be convexly curved in a direction toward the delivery portion 160.

In addition, the contact surface 160a may be curved so that the delivery portion 160 smoothly rotates the pressurization portion 120. For example, the contact surface 160a may be concavely curved in the direction toward the pressurization portion 120. Accordingly, the contact surface 160a may slide with respect to the one end 120a of the pressurization portion 120 to smoothly rotate the pressurization portion 120.

The second elastic member 170 may be pressurized by the delivery portion 160 and provide an elastic force to the delivery portion 160. For example, when the delivery portion 160 is pressurized by the aerosol generating article 200 in the first direction, the second elastic member 170 may be compressed to pressurize the delivery portion 160 in the second direction. Accordingly, when the force for pressurizing the delivery portion 160 in the first direction decreases or disappears, the second elastic member 170 may pressurize the delivery portion 160 in the second direction to restore the position of the delivery portion 160.

For example, the second elastic member 170 may include a spring, but is not limited thereto, and various elastic bodies following Hooke's Law may be included.

The user may insert the aerosol generating article 200 into the inside of the pressurization device 100 to inhale the aerosol.

The aerosol generating article 200 may pressurize the delivery portion 160 in the first direction so that the other end 120b of the pressurization portion 120 pressurizes the aerosol generating article 200.

The delivery portion 160 may move in the first direction by the aerosol generating article 200. When the delivery portion 160 moves in the first direction, the second elastic member 170 may be compressed by the delivery portion 160.

In addition, the delivery portion 160 may slide with respect to the pressurization portion 120 in the first direction to pressurize the pressurization portion 120 in the first direction. In other words, the contact surface 160a may pressurize the one end 120a of the pressurization portion 120 in the first direction while sliding along the one end 120a of the pressurization portion 120. Accordingly, the pressurization portion 120 may rotate in a direction in which the aerosol generating article 200 is pressurized, and the other end 120b of the pressurization portion 120 may pressurize the aerosol generating article 200.

The other end 120b of the pressurization portion 120 may pressurize the aerosol generating article 200 to induce the chemical reaction for generating the aerosol inside the aerosol generating article 200. The aerosol generating article 200 may generate the aerosol through the chemical reaction, and the user may inhale the generated aerosol.

On the other hand, the user may reduce the force for pressurizing the aerosol generating article 200 in order to extract the aerosol generating article 200 from the pressurization device 100.

The second elastic member 170 may restore the position of the delivery portion 160 to a state before the aerosol generating article 200 is inserted.

As an example, when the force of the user pressurizing the aerosol generating article 200 in the first direction decreases or disappears, the second elastic member 170 may move the delivery portion 160 in the second direction.

The delivery portion 160 may slide with respect to the pressurization portion 120 in the second direction to pressurize the pressurization portion 120 in the second direction. In other words, the contact surface 160a may pressurize the pressurization portion 120 in the second direction while sliding along the one end 120a of the pressurization portion 120. Accordingly, the pressurization portion 120 may rotate in a direction away from the aerosol generating article 200 and return to the position as illustrated in FIG. 4A.

As described above, the aerosol generating system 300 according to an embodiment may supply the aerosol to the user through a simple operation, and the user may easily prepare for reuse of the pressurization device 100.

FIG. 5A is a view illustrating an example wherein an aerosol generating article according to another embodiment is pressurized by a pressurization portion, and FIG. 5B is a view illustrating an example of a state after the aerosol generating article illustrated in FIG. 5A is pressurized by the pressurization portion.

The aerosol generating article 200 may include the aerosol generating substance. The aerosol generating substance may include a medium or liquid composition.

The medium may be a specific type of tobacco material. For example, the tobacco element may take a form of tobacco cut filler, tobacco particles, tobacco sheets, tobacco beads, or tobacco granules. In addition, the tobacco material may include, for example, one or more of tobacco leaves, tobacco side veins, puffed tobacco, tobacco cut filler, platelet cut filler, and reconstituted tobacco.

The liquid composition may include a tobacco extract. The tobacco extract may be a naturally generated nicotine or synthetic nicotine and may have any suitable weight concentration relative to the total solution weight of the liquid composition. For example, the tobacco extract may include freebase nicotine or nicotine-salt, but is not limited thereto.

The free base nicotine may mean neutral nicotine to which a proton is not added. For example, when a strong base such as ammonia (NH3) is added to a nicotine salt having a positive charge, the strong base is converted into a cation, and the nicotine salt may become a neutral nicotine base.

The liquid composition may include two or more types of nicotine salts. Nicotine salts may be formed by adding suitable acids, including organic or inorganic acids, to nicotine.

Acid for the formation of the nicotine salts may be appropriately selected in consideration of the rate of nicotine absorption in the blood, the flavor or savor, the solubility, or the like. For example, the acid for the formation of nicotine salts may be a single acid selected from the group consisting of benzoic acid, lactic acid, salicylic acid, lauric acid, sorbic acid, levulinic acid, pyruvic acid, formic acid, acetic acid, propionic acid, butyric acid, valeric acid, caproic acid, caprylic acid, capric acid, citric acid, myristic acid, palmitic acid, stearic acid, oleic acid, linoleic acid, linolenic acid, phenylacetic acid, tartaric acid, succinic acid, fumaric acid, gluconic acid, saccharic acid, malonic acid, and malic acid, or a mixture of two or more acids selected from the group, but is not limited thereto.

The liquid composition may include, for example, any one component of water, solvents, ethanol, plant extracts, spices, flavorings, and vitamin mixtures, or a mixture thereof.

The moisturizing agent may act as the aerosol former that is heated to generate an abundant amount of the aerosol. For example, the moisturizing agent may be glycerin, propylene glycol, or a mixture of components thereof, but is not limited thereto.

The spices may include menthol, peppermint, spearmint oil, and various fruit-flavored ingredients, but are not limited thereto.

The flavorings may include ingredients capable of providing various flavors or tastes to a user.

Vitamin mixtures may be a mixture of at least one of vitamin A, vitamin B, vitamin C, and vitamin E, but are not limited thereto.

In a case where a liquid composition is included in the aerosol generating article 200, the aerosol generating article 200 includes a carrier, and the liquid composition may be held on the carrier. Here, the 'carrier' refers to a structure that adsorbs and holds a fluid on a surface, or absorbs and holds a fluid inside thereof, and such expressions may be used below in the same manner.

The carrier may be a porous material, a polymer material, or a cellulose material. For example, the carrier may include cotton, sponge, ceramic, paper, glass, stainless steel, aluminum, polyethylene (PE), polypropylene, polyethylene terephthalate (PET), polytetrafluoroethylene (PTFE), or the like, but is not limited thereto.

The aerosol generating article may include a receiving portion 210. The receiving portion 210 may be a space inside the aerosol generating article 200 in which the chemical reaction occurs for generating the aerosol.

The aerosol generating article 200 may include a first substance and a second substance for generating the aerosol, different from that of the first substance.

As an example, the first substance may be a material that reacts with external air of the aerosol generating article 200 to generate heat, and the second substance may be the aerosol generating substance.

The first substance may be a material that reacts with air to generate heat. For example, the first substance may be a material that reacts with water vapor or gas contained in air. In detail, the first substance may be at least one selected from yellow phosphorus (P4), ethyl lithium (C2H5Li), dimethyl magnesium (C2H6MG), diethyl magnesium (C2H5Mg), dimethyl tin (C2H6Sn), diethyl zinc (C4H10Zn), dimethyl gallium (Ga(CH3)2), alkyl aluminum (CnH2n+1Al), alkyl lithium (CnH2n+1Li), and disilane (Si2H6), or a combination thereof.

The first substance may be disposed inside the receiving portion 210 in a state of being mixed with the second substance. In addition, the receiving portion 210 may be hermetically sealed. Accordingly, the receiving portion 210 may maintain a state where external air of the aerosol generating article 200 is not introduced before being pressurized by the pressurization portion 120.

The pressurization portion 120 may pressurize the aerosol generating article 200 to perforate at least a part of the aerosol generating article 200. For example, the aerosol generating article 200 may be perforated by including a point at the other end 120b of the pressurization portion 120.

If the aerosol generating article 200 is perforated, external air may be introduced into the receiving portion 210. The air introduced into the receiving portion 210 may react with the first substance, thereby inducing an exothermic reaction inside the aerosol generating article 200. Heat generated by the exothermic reaction may heat the second substance of the receiving portion 210 to generate the aerosol.

As described above, the user may introduce the external air into the inside of the aerosol generating article 200 by using the pressurization portion 120 to induce the exothermic reaction inside the aerosol generating article 200. Therefore, it is possible to inhale aerosol without using power.

On the other hand, while some components related to the present embodiment are illustrated in the aerosol generating article 200 illustrated in FIGS. 5A and/or 5B, it will be apparent to those skilled in the art to which the present embodiments belong that other general-purpose components may be further included in the aerosol generating article 200. For example, the aerosol generating article 200 may include a cooling element for cooling the aerosol or a filter element for filtering the aerosol, but is not limited thereto.

FIG. 6A is a view illustrating an aerosol generating article 200 according to another embodiment, and FIG. 6B is a view illustrating an example wherein the aerosol generating article 200 illustrated in FIG. 6A is pressurized by the pressurization portion 120.

Referring to FIGS. 6A and 6B, the aerosol generating article 200 according to another embodiment may include a receiving portion 210, a first chamber 220, and a second chamber 230.

The first chamber 220 may include a first substance, and the second chamber 230 may include a second substance different from the first substance. The first chamber 220 and the second chamber 230 may be, for example, in a form of a soft capsule or a hard capsule containing gelatin, glycerin, sorbitol, or the like, or a form including a carrier capable of holding a fluid.

The first chamber 220 or the second chamber 230 may be crushed, deformed, or moved by being pressurized by the pressurization portion 120, and accordingly, the chemical reaction may occur when the first substance and the second substance come into contact with each other.

As an example, the aerosol generating article 200 may include the first substance and the second substance that generate heat through the exothermic reaction by coming into contact with each other, and may include the aerosol generating substance inside the receiving portion 210.

For example, the first substance and the second substance may be at least one selected from chromium trioxide ($CrO_3$), ethyl alcohol ($C_2H_5OH$), carbon disulfide ($CS_2$), potassium permanganate ($KMnO_4$), ethylene glycol ($C_2H_6O_2$), sodium chlorite ($NaClO_2$), sulfuric acid ($H_2SO_4$), ether ($C_2H_5OC_2H_5$), sodium peroxide ($Na_2O_2$), and water ($H_2O$), or a combination thereof.

In detail, the combination of the first substance and the second substance may be sodium peroxide and water, sodium peroxide and carbon disulfide, chromium trioxide and ethyl alcohol, sodium chlorite and sulfuric acid, sodium chlorite and ether, potassium permanganate and ethylene glycol, or the like, but is not limited thereto.

When the first chamber 220 or the second chamber 230 is pressurized by the pressurization portion 120, the first substance and the second substance come into contact with each other, and the exothermic reaction may occur. For example, the pressurization portion 120 may pressurize the first chamber 220 and the second chamber 230 to crush the first chamber 220 and the second chamber 230.

If the first chamber 220 and the second chamber 230 are crushed, the first substance and the second substance are discharged to the outside of the first chamber 220 and the second chamber 230, respectively, so that they may come into contact with each other. The first substance and the second substance in contact may generate heat by the exothermic reaction, and the aerosol generating substance of the receiving portion 210 may be heated to generate the aerosol.

For example, the first substance may be sodium peroxide and the second substance may be water. Sodium peroxide and water may generate heat by reacting as in the following formula (1).

$$2Na_2O_2 + 2H_2O \rightarrow 4NaOH + O_2 \qquad \text{[Formula 1]}$$

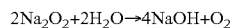

When sodium peroxide and water react, heat of 225 cal/g is generated based on the mass of sodium peroxide, and the generated heat may heat the aerosol generating substance to generate the aerosol. In addition, the generated aerosol may be discharged to the outside of the aerosol generating article 200 to reach the user.

As another example, the receiving portion 210 may contain the aerosol generating substance, the first substance included in the first chamber 220 is an acid source, and the second substance included in the second chamber 230 is a base source.

The acid source may be at least one selected from, for example, pyruvic acid, lactic acid, acetic acid, formic acid, 3-methyl-2-oxovaleic acid, 2-oxovaleic acid, 4-methyl-2-oxovaleic acid, 3-methyl-2-oxobutanoic acid, 2-oxooctanoic acid, and 2-oxopropanoic acid, or a combination thereof, but is not limited thereto.

The base source may be at least one selected from, for example, sodium carbonate ($Na_2CO_3$), sodium hydrogen carbonate ($NaHCO_3$), sodium hydroxide ($NaOH$), and potassium hydroxide ($KOH$), or a combination thereof, but is not limited thereto.

Sodium carbonate ($Na_2CO_3$) or sodium hydrogen carbonate ($NaHCO_3$) may be included in the second substance as the base source.

In this case, the first chamber 220 or the second chamber 230 is pressurized by the pressurization portion 120, and thereby the acid source as the first substance and the base source as the second substance may react with each other to generate carbon dioxide ($CO_2$). The generated carbon dioxide may pass through the aerosol generating substance of the receiving portion 210 to generate the aerosol on the inside of the aerosol generating article 200. The generated aerosol may be discharged to the outside of the aerosol generating article 200 to reach the user.

Sodium hydroxide ($NaOH$) or potassium hydroxide ($KOH$) may be included in the second substance as the base source, and free base nicotine may be included in the aerosol generating substance of the receiving portion 210.

In this case, the first chamber 220 or the second chamber 230 is pressurized by the pressurization portion 120, and thereby the acid source as the first substance and the free base nicotine may come into contact with each other to generate nicotine salt. In addition, the base source as the second substance and free base nicotine as the aerosol generating substance may come into contact with each other to cause the exothermic reaction. Accordingly, the aerosol is generated inside the aerosol generating article 200, and the generated aerosol may be discharged to the outside of the aerosol generating article 200 to reach the user.

As described above, the user may use to the pressurization portion 120 to pressurize the first chamber 220 and the second chamber 230, thereby inducing the chemical reaction inside the aerosol generating article 200. Therefore, the user may easily inhale the aerosol without using power.

FIG. 7A is a view illustrating an aerosol generating article 200 according to another embodiment, and FIG. 7B is a view illustrating an example of another aspect in which the aerosol generating article 200 according to the embodiment is pressurized by the pressurization portion 120.

Referring to FIGS. 7A and 7B, the aerosol generating article 200 may include the receiving portion 210, the first chamber 220, the second chamber 230, and a partition portion 240.

The aerosol generating article 200 of FIGS. 7A and/or 7B may be the aerosol generating article 200 to which the partition portion 240 is added in the aerosol generating article 200 illustrated in FIG. 6A, and hereinafter, redundant descriptions will be omitted.

The first chamber 220 may include a material having elasticity and may be deformed by an external force. When the first chamber 220 is pressurized, the first chamber 220 may deform to apply pressure to the first substance contained therein.

The first chamber 220 and the second chamber 230 may be disposed adjacent to each other. For example, the first chamber 220 and the second chamber 230 may be disposed side by side in a longitudinal direction of the aerosol generating article 200.

The partition portion 240 may be disposed between the first chamber 220 and the second chamber 230 to prevent the first substance and the second substance from coming into contact with each other. For example, the first chamber 220 may be disposed on one side of the partition portion 240, and the second chamber 230 may be disposed on the other side of the partition portion.

The partition portion 240 may be a permeable membrane that transmits a substance when subjected to pressure. For example, the partition portion 240 may include holes having a fine size, and may be pressurized to transmit the first substance or the second substance.

When the first chamber 220 is pressurized by the pressurization portion 120, the first chamber 220 may be deformed to pressurize the first substance contained therein in a direction toward the second chamber 230.

The first substance pressurized by the first chamber 220 may transmit the partition portion 240 and reach the second chamber 230. The first substance reaching the second chamber 230 may come into contact with the second substance to generate the chemical reaction, and the aerosol may be generated inside the aerosol generating article 200.

An amount of the first substance transmitting the partition portion 240 may vary depending on the pressure applied to the first chamber 220. For example, as the pressurization portion 120 strongly pressurizes the first chamber 220, the first chamber 220 may strongly pressurize the first substance in a direction toward the second chamber 230. Accordingly, the chemical reaction inside the aerosol generating article 200 may be further promoted by increasing the amount of the first substance transmitting through the partition portion 240.

In other words, the user may adjust the pressure at which the pressurization portion 120 pressurizes the first chamber 220, and adjust the amount of the first substance transmitting to the second chamber 230, so that the amount of aerosol generated on the inside of the aerosol generating article 200 may be controlled.

As described above, the user uses the pressurization portion 120 to pressurize the first chamber 220 so that the first substance transmits through the partition portion 240. Therefore, the chemical reaction inside the aerosol generating article 200 is induced and thereby the user may easily inhale the aerosol.

FIG. 8A is a view illustrating an aerosol generating article according to another embodiment, and FIG. 8B is a view illustrating an example wherein the aerosol generating article 200 illustrated in FIG. 8A is pressurized by the pressurization portion 120.

Referring to FIGS. 8A and 8B, the aerosol generating article 200 according to an embodiment may include the receiving portion 210, the first chamber 220, and the second chamber 230.

The aerosol generating article 200 of FIG. 8A and/or FIG. 8B may be an aerosol generating article 200 in which a disposition structure of the first chamber 220 and the second chamber 230 is changed in the aerosol generating article 200 of FIG. 6A, and hereinafter, redundant descriptions will be omitted The first chamber 220 and the second chamber 230 may be disposed to be spaced apart from each other. For example, the first chamber 220 may be disposed to surround the second chamber 230 by being spaced apart from the second chamber 230. In addition, the second chamber 230 may be disposed to surround the receiving portion 210.

The pressurization portion 120 may pressurize the aerosol generating article 200 to allow the first chamber 220 and the second chamber 230 to come into contact with each other. For example, the pressurization portion 120 may pressurize an outer surface of the aerosol generating article 200 to move the first chamber 220 in a direction toward the second chamber 230, and allow the first chamber 220 and the second chamber 230 to come into contact with each other.

As an example, the first chamber 220 and the second chamber 230 may each include a carrier, and the each carrier may hold the first substance and the second substance in a fluid state. Accordingly, when the first chamber 220 and the second chamber 230 come into contact with each other, the first substance or the second substance seeps out of the first chamber 220 or the second chamber 230, and thereby the first substance and the second substance may come into contact with each other.

When the first substance and the second substance come into contact with each other, the chemical reaction may occur inside the aerosol generating article 200, and the aerosol may be generated inside the aerosol generating article 200.

As described above, the user may use the pressurization portion 120 to move the first chamber 220, and allow the first chamber 220 and the second chamber 230 to come into contact with each other, thereby inducing the chemical reaction inside the aerosol generating article 200. Accordingly, the user may easily inhale the aerosol without using power.

Those of ordinary skill in the art related to the present embodiments may understand that various changes in form and details can be made therein without departing from the scope of the present disclosure. The disclosed methods should be considered in a descriptive sense only and not for purposes of limitation. All differences within the scope of equivalents should be construed as being included in the present disclosure.

What is claimed is:

1. A pressurization device for pressurizing an aerosol generating article, the pressurization device comprising:
 a pressurization portion that is configured to induce a chemical reaction that generates an aerosol inside the aerosol generating article by moving when the aerosol generating article is inserted into the pressurization device and pressurizing the aerosol generating article accommodated inside the pressurization device.

2. The pressurization device of claim 1, wherein one end of the pressurization portion is configured to receive the force applied by the aerosol generating article, such that the pressurization portion rotates and another end of the pressurization portion pressurizes the aerosol generating article.

3. The pressurization device of claim 1, further comprising a central shaft that penetrates the pressurization portion,
 wherein the pressurization portion rotates about the central shaft.

4. The pressurization device of claim 1, further comprising an elastic member that is configured to pressurize the pressurization portion in a direction opposite to a direction in which the force is applied by the aerosol generating article to the pressurization portion.

5. The pressurization device of claim 1, wherein one end of the pressurization portion is configured to be:
 deformed by the aerosol generating article, when the aerosol generating article is inserted into the pressurization device, such that another end of the pressurization portion moves in a direction toward the aerosol generating article, and restored to an initial shape, when the aerosol generating article is extracted from the pressurization device, such that the other end of the pressurization portion moves in a direction away from the aerosol generating article.

6. The pressurization device of claim 1, further comprising: a delivery portion that is configured to be pressurized by the aerosol generating article, such that the delivery portion moves and applies a force to the pressurization portion, wherein the pressurization portion is configured to rotate, due to the force applied by the delivery portion, such that the pressurization portion pressurizes the aerosol generating article.

7. The pressurization device of claim 6, wherein the delivery portion is in contact with the pressurization portion, and is configured to slide with respect to the pressurization portion to rotate the pressurization portion.

8. The pressurization device of claim 7, wherein one surface of the delivery portion that is in contact with the pressurization portion is curved, such as to cause the pressurization portion to rotate by allowing the delivery portion to slide with respect to the pressurization portion.

9. The pressurization device of claim 6, further comprising: an elastic member that is configured to pressurize the delivery portion in a direction opposite to a direction in which the aerosol generating article pressurizes the delivery portion.

10. An aerosol generating system comprising:

an aerosol generating article that comprises a first substance and a second substance for generating an aerosol, the second substance being different from the first substance; and a pressurization device that comprises a pressurization portion that is configured to be moved by a force applied by the aerosol generating article such that the pressurization portion pressurizes the aerosol generating article to induce a chemical reaction in at least one from among the first substance and the second substance.

11. The aerosol generating system of claim 10, wherein the pressurization portion is configured to perforate at least a part of the aerosol generating article so that external air is introduced into the aerosol generating article, and wherein the first substance is configured to come into contact with the external air that is introduced into the aerosol generating article, such as to generate heat that heats the second substance.

12. The aerosol generating system of claim 10, wherein the aerosol generating article further comprises a first chamber containing the first substance, and a second chamber containing the second substance, and wherein the pressurization portion is configured to pressurize at least one from among the first chamber and the second chamber, and allow the first substance and the second substance to come into contact with each other to induce the chemical reaction.

13. The aerosol generating system of claim 12, wherein the first chamber and the second chamber are disposed adjacent to each other, and wherein the aerosol generating article further comprises a partition portion disposed between the first chamber and the second chamber, the partition portion configured to prevent contact between the first substance and the second substance.

14. The aerosol generating system of claim 13, wherein the pressurization portion is configured to pressurize at least one from among the first chamber and the second chamber so that the first substance or the second substance transmits through the partition portion.

15. The aerosol generating system of claim 12, wherein the first chamber and the second chamber are spaced apart from each other, and wherein the pressurization portion is configured to pressurize the first chamber in a direction toward the second chamber so that the first substance and the second substance come into contact with each other.

16. The pressurization device of claim 1, wherein the one end of the pressurization portion is a material having elasticity.

17. The aerosol generating system of claim 13, wherein the first chamber and the second chamber are disposed side by side in a longitudinal direction of the aerosol generating article.

18. The aerosol generating system of claim 13, wherein the partition portion is a permeable membrane having holes and configured to transmit the first substance or the second substance when subjected to pressure.

19. The aerosol generating system of claim 13, wherein the first chamber is disposed to surround the second chamber and is spaced apart from the second chamber.

* * * * *